United States Patent [19]

Cardiff et al.

[11] Patent Number: 4,775,620

[45] Date of Patent: Oct. 4, 1988

[54] CYTOKERATIN TUMOR MARKERS AND ASSAYS FOR THEIR DETECTION

[75] Inventors: Robert D. Cardiff, Davis; Paul V. Rossitto, Sacramento, both of Calif.; Alan C. Brabon, Andrews Air Force Base, Md.

[73] Assignee: The Regents of the University of California, Berkeley, Calif.

[21] Appl. No.: 696,284

[22] Filed: Jan. 30, 1985

Related U.S. Application Data

[63] Continuation-in-part of Ser. No. 568,862, Jan. 6, 1984, abandoned.

[51] Int. Cl.[4] .................. G01N 33/53; G01N 33/574; G01N 33/577
[52] U.S. Cl. ......................................... 435/7; 435/29; 435/68; 435/172.2; 435/810; 436/519; 436/548; 436/813; 530/387; 530/828; 935/110
[58] Field of Search ................... 435/7, 29, 68, 172.2, 435/948, 810; 436/519, 547, 548, 804, 808, 813; 935/103, 110; 260/112 B, 112 R; 530/387, 828

[56] References Cited

U.S. PATENT DOCUMENTS 4,229,426 10/1980 Haagensen ........................ 436/813

FOREIGN PATENT DOCUMENTS 0118365 9/1984 European Pat. Off. .

OTHER PUBLICATIONS

Brabon et al. (1983) Monoclonal Antibodies to Estrogen Sensitive Proteins in Human Breast Cancer Cells, Abstract presented at Breast Cancer Research Conference, Mar. 20-24, 1983, Internat'l. Assoc. Breast Ca. Research.
Karsten et al. (1983) Monoclonal Antibodies Against Antigens of the Human Mammary Carcinoma Cell Line MCF-7, Abstract Arch Geschwulstforsch 53(6): 529-536.
Moll et al. (1982) The Catalog of Human Cytokeratins: Patterns of Expression in Normal Epithelial, Tumors and Cultured Cells, Cell 31: 11-24.
Debus et al. (1982) Monoclonal Cytokeratin Antibodies that Distinguish Simple from Stratified Squamous Epithelia: Characterization on Human Tissues, Eur. Mol. Biol. Organ. 1(12): 1641-1648, Biol. Abstr. 76(4): 29367.
Debus et al. (1984) Immunohistochemical Distinction of Human Carcinomas by Cytokeratin Typing with Monoclonal Antibodies, Am. J. Pathol. 114(1): 121-130, Biol. Abstr. 77(11): 84821.
Van Muijen et al. (1984) Monoclonal Antibodies with Different Specificities Against Cytokeratins: An Immunochemical Study of Normal Tissues and Tumors, Am. J. Pathol. 114(1): 9-17, Biol. Abstr. 77(12): 93017.
Krepler et al. (1981) Keratin-Like Proteins in Normal and Neoplastic Cells of Human and Rat Mammary Gland as Revealed by Immunofluorescence Differ. 20(3) 242-252.
Krepler et al. (1982) Antibodies to Intermediate Filament Proteins as Molecular Markers in Clinical Tumor Pathology, Differentiation of Carcinomas by Their Reaction with Different Cytokeratin Antibodies, Pathol. Res. Pract. 175(2): 212-226 (Abstr.).
Coggi et al. (1982) Cytokeratin Immunohistochemistry in Human Neoplastic Cells, Biol. Cell 45(2):202 (Abstr.).
Köhler and Milstein (1975) Continuous Cultures of Fused Cells Secreting Antibody of Predefined Specificity, Nature 256:495-497.
Westley and Rochefort (1980) Cell 20:3353-3362.
Veith et al. (1983) Cancer Res. 43:1861-1868.
Ciocca et al. (1982) Cancer Res. 42:4256-4258.
Wagner et al. (1982) Aust. N.Z.J. Surg. 52:41-43.
Mross et al. (1983) Klin. Wochenschr. 61:461-468.
Mairesse et al. (1981) J. Steroid Biochem. 15:375-381.
Madri et al. (1983) Lab. Invest. 48:98-107.
F. Ramaekers et al. (1981) Use of Antibodies to Intermediate Filaments in the Characterization of Human Tumors, Cold Spring Harb. Symp. Quant. Biol. 46:331-340.
M. Osborn et al. (1982) Intermediate Filaments: Cell-Type-Specific Markers in Differentiation and Pathology, Cell 31:303-306.
M. Osborn et al. (1984) Conventional and Monoclonal Antibodies to Intermediate Filament Proteins in Human Tumor Diagnosis In: Cancer Cells 1, The Transformed Phenotype, Cold Spring Harbor Laboratory, pp. 191-200.
T. T. Sun et al. (1984) Classification, Expression and Possible Mechanisms of Evolution of Mammalian Keratins: A Unifying Model In: Cancer Cells 1, The Transformed Phenotype, Cold Spring Harbor Laboratory, pp. 169-176.
M. Osborn et al. (1984) Uses of Conventional and Monoclonal Antibodies to Intermediate Filament Proteins in the Diagnosis of Human Tumors, (Proc. 4th Internat. Expert Meeting of the Deutsche Stiftung fuer Krebsforschung.) In: Genes and Antigens in Cancers Cells-The Monoclonal Antibody Approach, Contributions to Oncology 19:148-159.
B. Luening et al. (1983) Sequence Homology Between Tissue Polypeptide Antigen (TPA) and Intermediate Filament (IF) Proteins, Acta. Chem. Scand. Ser. B 37:731-733.
P. Redelius et al. (1980) Chemical Studies of Tissue Polypeptide Antigen (TPA), II. Partial Amino Acid (List continued on next page.)

Primary Examiner—Sidney Marantz
Attorney, Agent, or Firm—Leydig, Voit & Mayer

[57] ABSTRACT

Methods and compositions are provided for identifying patients suffering from neoplastic diseases such as breast cancer. It has been found that neoplastic epithelial cells, including neoplastic mammary epithelial cells, release a particular N-terminal blocked, soluble cytokeratin into circulation. The presence of this cytokeratin is diagnostic of neoplastic disease.

34 Claims, No Drawings

OTHER PUBLICATIONS

Sequences of Cyanogen Bromide Fragments of TPA Subunit $B_1$1, Acta Chemica, Scandinavica B 34:265-273.

J. A. Madri et al. (1983) Methods in Laboratory Investigation, Use of Avidin-Biotin Complex in an ELISA System: A Quantitative Comparison with Two Other Immunoperoxidase Detection Systems Using Keratin Antisera, Lab. Invest. 48:98-0107.

M. Altmannsberger et al. (1981) The Distribution of Keratin Type Intermediate Filaments in Human Breast Cancer, Virchows Arch. (Cell Pathol.) 37:277-284.

W. W. Franke et al. (1981) Diversity of Cytokeratins, Differentiation Specific Expression of Cytokeratin Polypeptides in Epithelial Cells and Tissues, J. Mol. Biol. 153:933-959.

F. C. S. Ramaekers et al. (1983) Antibodies to Intermediate Filament Proteins in the Immunohistochemical Identification of Human Tumors: An Overview, Histochem. J. 15:691-713.

F. Ramaekers et al. (1983) Monoclonal Antibody to Keratin Filaments, Specific for Glandular Epithelia and Their Tumors: Use in Surgical Pathology, Lab. Invest 49:353-361.

J. Viac et al. (1983) Reactivity Pattern of a Monoclonal Antikeratin Antibody (KL1), J. Invest. Dermat. 81:351-354.

CYTOKERATIN TUMOR MARKERS AND ASSAYS FOR THEIR DETECTION

This application is a continuation-in-part of application Ser. No. 568,862 filed on Jan. 6, 1984, now abandoned.

BACKGROUND OF THE INVENTION

1. Field of the Invention

The ability to detect and diagnose cancer through the identification of tumor markers is an area of widespread interest. Tumor markers are substances, typically proteins, glycoproteins, polysaccharides, and the like, which are produced by tumor cells and characteristic thereof. Often, a tumor marker is produced by normal cells as well as tumor cells. In the tumor cell, however, the production is in some way atypical. For example, production of the tumor marker may be greatly increased in the cancer cell. Alternatively, proteins and other substances normally present within or on the surface of normal cells may be released or shed into circulation when the cell becomes malignant. Detection of such secreted substances in serum may thus be diagnostic of the malignancy.

Another problem encountered in cancer diagnosis relates to identifying the cellular origin of both primary and metastatic tumors. With both types of tumors, it is sometimes difficult to morphologically distinguish among tumors of differing cellular origins, e.g., tumors of epithelial origin (carcinomas), tumors originating in the non-epithelial connective tissue (sarcomas) and lymphoid tumors (lymphomas) Moreover, with breast epithelial cancers, it is often difficult to distinguish among tumors originating in ductal epithelial tissues, secretory epithelial tissues, and myoepithelial tissues.

Therefore, it is desirable to identify previousy unrecognized tumor markers, particularly tumor markers which are secreted into circulation and which may be identified by serum assays. It is also desirable to develop methods and compositions which allow determination of the cellular origin of a particular tumor. 2. Description of the Prior Art A 52,000 dalton protein released by certain breast cell lines in response to estradiol stimulation has been identified. See, Westley and Rochefort (1980) Cell 20:353-3362, and Veith et al. (1983) Cancer Res. 43:1861-1868. Monoclonal antibodies raised against the MCF-7 human breast cancer cell line have been shown to identify a 24 kilodalton cytosol protein. Ciocca et al. (1982) Cancer Res. 42:4256-4258. A protein referred to as tissue polypeptide antigen (TPA) is related to cytoplasmic intermediate filaments of epithelial cells. TPA is reported to be a tumor marker, both in serum and as a cell surface marker. See, Altmannsberger et al. (1981) Virchows Arch. [Cell Pathol.] 37:277-284, where breast carcinoma cells reacted with antibodies to prekeratin; Wagner et al. (1982) Aust. N.Z.J. Surg. 52:41-43, where elevated serum levels of TPA were detected in some patients suffering from gastric and colorectal carcinomas; Mross et al. (1983) Klin. Wochenschr. 61:461-468, where elevated serum TPA levels were found in some patients suffering from breast cancer; and Luning and Nilsson (1983) Acta Chemica Scandinavica 37:731-753, where partial sequence homology between TPA and certain filamentous proteins, including epidermal keratins, was reported. Sangtec Medical, Bromma, Sweden, sells a kit for the detection of TPA in serum and plasma under the tradename Prolifigren ® RIA kit. Mariresse et al. (1981) J. Steroid Biochem. 15:375-381, report the presence of an approximately 50 kd low-turnover rate protein in the culture medium of MCF-7 cells. Serologic detection of keratin has been reported in a cancer patient. Madri et al. (1983) Lab. Invest. 48:98-107.

SUMMARY OF THE INVENTION

The present invention provides methods and compositions useful for detecting and monitoring primary and metastatic epithelial tumors, particularly epithelial breast tumors. The method relies on the detection of extracellular cytokeratins which are released into circulation by neoplastic epithelial cells. The extracellular cytokeratins have a molecular weight of approximately 40 to 46 kilodaltons and are related to approximately 42 to 48 kd proteins found on the cell surface of neoplastic epithelial cells. Both the extracellular cytokeratins and the cell surface proteins are in turn related to intracellular cytokeratin, but the extracellular cytokeratin differs from both the intracellular cytokeratin and cell surface cytokeratin in that it has a blocked N-terminus and is soluble in aqueous solution. Detection of the extracellular cytokeratin may be conveniently accomplished by reaction with monoclonal antibodies derived from hybridoma cell lines UCD/AB 6.11, UCD/PR 10.11, or other antibodies having a similar specificity, and determining the formation of specific complexes.

The compositions of the present invention are also useful for identifying the cellular origin of various epithelial tumors. Monoclonal antibodies capable of reacting with epithelial cytokeratins, particularly UCD/PR 10.11, may be utilized to distinguish epithelial tumors (carcinomas) from non-epithelial tumors such as sarcomas and lymphomas. Moreover, groups or panels of antibodies may be utilized to distinguish among primary and metastatic breast tumors of ductal epithelial, secretory epithelial, and myoepithelial origin. Extracellular soluble cytokeratins secreted by neoplastic epithelial cells substantially free from other serum proteins are also part of the present invention.

DESCRIPTION OF THE SPECIFIC EMBODIMENTS

Methods and compositions are provided for the detection, identification, and monitoring of epithelial tumors, particularly mammary epithelial tumors. It has been found that both normal and neoplastic epithelial cells are characterized by the presence of an about 42 to 48 kilodalton (kd) protein on the cell surface, which protein is immunologically and compositionally related to intracellular cytokeratin. It has also been found that a smaller form of the cytokeratin-related protein (about 40 to 46 kd; is released by both normal and neoplastic cells, but that the rate of release from neoplastic cells is significantly higher. Thus, a patient population may be screened for epithelial neoplasms by assaying for the presence of such extracellular cytokeratins in serum. The assay is particularly suitable for monitoring the progress of patients undergoing treatment for epithelial neoplasms.

Intermediate filaments are a major component of the cytoskeleton in many types of cells. Epithelial cells of tissues such as the mammary gland contain soluble intermediate filaments composed of keratin. These proteins, referred to as cytokeratins, are found in both normal and neoplastic mammary cells and comprise a group of at least 19 distinct proteins, referred to as Types 1 through 19 (Moll et al. (1982) Cell 31:11). Heretofore, such cytokeratins have been believed to be intracellular cytoskeletal proteins. The work reported in the Experimental section hereinafter, however, demonstrates that proteins which are immunologically and compositionally related to such intracellular cytokeratins can also be found on the cell surface and be secreted from the cells.

The cell surface cytokeratin and extracellular cytokeratin identified by the present invention are structurally and immunologically related to, but not identical, to known intracellular cytokeratins. Structurally related means that there is at least 60% homology between the extracellular/cell surface cytokeratins and the intracellular cytokeratins, usually being 75% or greater homology. Immunologically related means that there will be at least one common epitopic site among the cytokeratins, usually being a plurality of epitopic sites, but fewer than all epitopic sites. In the exemplary case of breast epithelial cells, it is found that there are at least three epitopes present on the cell surface cytokeratin which are immunologically cross-reactive with Types 8, 18 and 19 intracellular cytokeratins. The extracellular cytokeratin which is released from breast epithelial cells is most strongly cross-reactive with Type 8 and Type 18 intracellular cytokeratin and is soluble in aqueous solution. It is further found that the extracellular cytokeratin has a blocked N-terminus.

Detection of the extracellular cytokeratin in a biological fluid, such as serum, can be related to the status of an epithelial carcinoma. Neoplastic epithelial cells release the cytokeratin at an increased rate relative to normal epithelial cells, and observing the serum level of cytokeratin can be related to the status of the disease. For example, serum levels of cytokeratins will be expected to decrease after a tumor is surgically removed or regression is induced by other forms of therapy. Serum levels of the patient can subsequently be monitored to detect increased levels of extracellular cytokeratins which would be diagnostic of an increased tumor load, either primary or metastic.

The present invention is also useful for screening tumor cells to determine the cellular origin of the tumor cells. The presence of cytokeratins in the tumor cells is diagnostic of the epithelial origin of the cells. Thus, epithelial tumors may be distinguished from non-epithelial tumors by reaction with antibody specific for the cell cytokeratins. Moreover, it has been found that certain antibodies reactive with cytokeratins are able to distinguish among ductal epithelial, secretory epithelial, and myoepithelial breast cells. Thus, by employing a group or panel of antibodies (typically package as a kit) which are reactive with each type of epithelial breast cell, but substantially less reactive with the other two types of epithelial breast cell, the cellular origin of a breast tumor may be determined, conveniently by histochemical staining techniques. By substantially less reactive, it is meant that it will be possible to evaluate positive and negative samples based on reactivity with the antibody by means of conventional techniques. Knowledge of the cellular origin of a tumor is useful in selecting the proper mode of therapy.

A typical kit for screening serum or neoplastic epithelial cells to determine the origin of such cells would contain antibody reactive with ductal epithelial cells but being substantially less reactive with secretory epithelial cells and myoepithelial cells, antibody reactive with secretory epithelial cells but being substantially less reactive with ductal epithelial cells and myoepithelial cells, or antibody reactive with myoepithelial cells but being substantially less reeactive with ductal epithelial cells and secretory epithelial cells and means for detecting the reaction of the antibodies with the neoplastic epithelial cells or cell markers. The epithelial cells are typically mammalian epithelial cells. In preferred embodiments of the invention at least one of the antibodies is UCD/PR 10.11 or UCD/AB 6.11.

Conveniently, the presence of the cell cytokeratins and the extracellular cytokeratins may be determined immunologically employing conventional immunoassays or histochemical staining techniques using antibodies reactive with the proteins. Such antibodies can be prepared conventionally (as described below) employing either the cell cytokeratins or extracellular cytokeratins, or antigenic fragments thereof, as the immunogen. Conveniently, whole or lysed cells from breast tumor cell lines may be employed as the immunogen. Alternatively, antibodies specific for the cytokeratins may be utilized to isolate the cytokeratins from serum, primary tumor cells, or tumor cell lines, to obtain purified antigen substantially free from other serum proteins for use as the immunogen.

Antibodies may be obtained by injecting the desired immunogen into a wide variety of vertebrates in accordance with conventional techniques. Suitable vertebrates include mice, rats, sheep and goats, in particular mice. Usually, the animals are bled periodically with successive bleeds having improved titer and specificity. The antigens may be injected intramuscularly, intraperitoneally, subcutaneously, or the like. Usually, a vehicle is employed such as complete or incomplete Freund's adjuvant. If desired, monoclonal antibodies can be prepared.

To obtain monoclonal antibodies, spleen cells from the immunized vertebrate are immortalized. The manner of immortalization is not critical. Presently, the most common method is fusion with a myeloma fusion partner. Other techniques include EBV transformation, transformation with bare DNA, e.g., oncogenes, retroviruses, etc., or any other method which provides for stable maintenance of the cell line and production of monoclonal antibodies. Human monoclonal antibodies may be obtained by fusion of the spleen cells with an appropriate human fusion partner, such as WI-L2, described in European application no. 82.301103.6, the relevant portions of which are incorporated herein by reference. A detailed technique for producing mouse×-mouse monoclonal antibodies is taught by Oi and Herzenberg, in "Selected Methods in Cellular Immunology," Mishell and Shiigi (eds.), W. H. Freeman and Co., San Francisco (1980) pp 351-372. The antibodies of the present invention may be of any immunoglobulin class, i.e., IgG, including IgG1, IgG2a, and IgG2b, IgA, IgD, IgE and IgM, usually being IgG or IgM.

Particularly useful monoclonal antibodies have been prepared for use in the present invention. Antibody UCD/AB 6.11 is reactive with the intracellular, cell surface, and extracellular forms of epithelial cytokeratins, particularly with Type 18 cytokeratin which is characteristic of secretory epithelial cells. Antibody UCD/PR 10.11 is reactive with intracellular and extracellular forms of cytokeratin, particularly with Type 8 cytokeratins which are characteristic of ductal epithelial cells. UCD/PR 7.01 is reactive with intracellular and extracellular forms of an antigen which is characteristic of myoepithelial cells. These three antibodies are particularly suitable for screening neoplastic epithelial cells to determine whether they are of ductal, secretory, or myoepithelial origin.

Antibody UCD/PR 10.11 is also particularly suitable for screening tumor cells to determine if they are of epithelial origin. It is found that the UCD/PR 10.11 antibody has a high affinity for epithelial cells and provides highly specific staining with very low background levels.

Once antibodies having suitable specificity have been prepared, a wide variety of immunological assay methods are available for determining the formation of specific antibody-anti-complexes. Numerous competitive and non-competitive protein binding assays have been described in the scientific and patent literature, and a large number of such assays are commercially available. Exemplary immunoassays which are suitable for detecting the serum antigen include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

It will usually be necessary to pretreat the biological sample in some manner prior to performing the immunoassay. Sample preparation will vary depending on the source of the biological sample. Solid tumors and other tissue samples will be prepared by lysing the cells. Serum samples will typically be prepared by clotting whole blood and isolating the supernatant in accordance with well known methods. Other biological fluids, such as semen, sputum, and urine, may also be assayed for the presence of the extracellular cytokeratin.

Conventional immunohistochemical staining techniques may also be used for detecting the cytokeratins in tissue samples. For example, the tissue sample may be fixed in formalin, B-5 or other standard histological preservatives, dehydrated and embedded in paraffin as is routine in any hospital pathology laboratory. Sections may be cut from the paraffin and mounted on glass slides. The cellular antigen can then be detected and localized either by exposure to labelled antibody and a labelled secondary antibody. Alternatively, cytological preparations may be used. For example, cells from the tissue sample may be fixed on a slide, typically by exposure to formalin in a buffer at physiologic pH followed by suspension in acetone and pelleting onto gelatin-coated slides by centrifugation. The cell surface receptor may then be localized, either by exposure to labelled antibody or by exposure to unlabelled antibody and a labelled secondary antibody. The amount of the cell surface protein in the sample is directly proportional to the amount of bound label.

Whole body imaging techniques employing radioisotope labels can be utilized for locating epithelial tumors, particularly breast carcinomas which have metastasized. The antibodies of the present invention, or fragments thereof, are bound to a suitable radioisotope, typically technetium-99, $^{123}$iodine, $^{125}$iodine, or $^{131}$iodine, or a combination thereof, and administered parenterally. The biodistribution of the label is monitored by scintigraphy, and accumulations of the label may be related to the presence of estrogen-sensitive neoplastic mammary epithelial cells. Whole body imaging techniques are described in U.S. Pat. Nos. 4,036,945 and 4,311,688, the disclosures of which are incorporated herein by reference.

The following experiments are offered by way of illustration and not by way of limitation.

EXPERIMENTAL

The following abbreviations are used:
BSA—bovine serum albumin
DCC—dextran-coated charcoal
ER—estrogen receptor
HMFGM—human milk fat globule membrane
IEF—isoelectric focusing
MCA—monoclonal antibody
PBS—phosphate-buffered saline (0.01 M sodium phosphate, pH 7.3, containing 0.15 M NaCl)
RIA—radioimmunoassay
SDS-PAGE—sodium dodecyl sulfate-polyacrylamide gel electrophoresis

MATERIALS AND METHODS

Cell Lines

1. MCF-7 cells. The MCF-7 human mammary tumor cell line was used to both immunize and screen for antibody production. This is a well characterized cell line that was derived from a pleural effusion of a patient with metastatic breast cancer (Soule et al. (1973) J. Natl. Cancer Res. 51:1409–1416). It has been shown to contain both estrogen and progesterone receptors.

2. HBL-100. HBL-100 is a non-malignant human breast epithelial cell line developed from lactating breast milk sample (Polanowski et al. (1976) In Vitro 12:328–336). It does not contain estrogen receptors.

3. 186-NWT. 186-NWT is a human epithelial cell line developed from ascites fluid from a patient with metastatic breast cancer. It has not shown any breast cell markers and is ER negative.

4. P3x63Ag8.653. This is a mouse myeloma cell line used as a hybridoma fusion partner for MCA production. It does not produce immunoglobulin or any immunoglobulin subunits (Kearney et al. (1979) J. Immunol. 123:1548–1555).

Growth Media

Hybridoma cell lines were grown in Roswell Park Memorial Institute Tissue Culture Medium 1640 (Gibco Laboratories, Grand Island, N.Y.) supplemented with 10% heat inactivated calf serum, 1 mM sodium pyruvate, 0.1 mM nonessential amino acids, 2 mM L-glutamine, and 25 µg/ml gentamicin. Human breast cell lines were maintained in Dulbecco's Modified Eagle's Minimal essential medium with either 5% calf or horse serum, 1 µg/ml insulin, 25 µg/ml gentamicin and 100 nM 17β-estradiol (Sigma Chemical Co., St. Louis, Mo.).

5. Cell line AE1 is a hybridoma cell line described by Tseng et al. (1982) Cell 30:361–372, which was prepared by immunization with cytokeratins. The antibodies produced by the cell line are specific for all acidic cytokeratins and specifically for MCF-7 Type 19.

6. Cell line βH11 is a hybridoma cell line described by Gown and Vogel (1982) J. Cell Biol. 95:414–424, which was prepared by immunization with cytokeratin. The antibodies produced by the cell line are specific for cytokeratin Type 8, 18 and 19 in MCF-7 cells.

Tissue Specimens

Paraffin blocks of normal and malignant human breast tissue were obtained from the School of Medicine, Department of Pathology, University of California Medical Center, Sacramento, California.

Human Milk Fat Globule Membranes

Delipidated HMFGM was prepared by extracting the cream fraction of human milk with chloroform and ether (Ceriani et al. (1977) Proc. Nat. Acad. Sci. U.S.A. 74:582–586).

Monoclonal Antibody Production

A standard polyethylene glycol fusion, hypoxanthine-aminopterin-thymidine selection procedure as described by Oi and Herzenberg (1980) in: Selected Methods in Cellular Immunology, Mishell and Shiigi, eds., W. H. Freeman and Co., San Francisco, CA pp. 351–372. Antibody producing clones were identified with radioiodinated rabbit anti-mouse IgG by solid phase RIA and autoradiography as described by Tsu and Herzenberg (1980) id. pp.373–397.

BALB/c mice were hyperimmunized with live intact MCF-7 cells ($2 \times 10^6$ cells) intraperitoneally once per week for three weeks. After three weeks, the mice were immunized a fourth time with $2 \times 10^6$ cells intraperitoneally three days prior to the fusion. Mouse spleen cells were then hybridized with P3x63Ag8.653 mouse myeloma cells.

Whole live MCF-7 and HBL-100 cells were also used in solid phase RIA for first and second level screening (Brown et al. (1979) J. Immunol. Methods 31:201–209). Live cells were used to avoid selecting for fixation artifacts. MCF-7 was used as a positive screen to identify antibodies against antigens on ER positive cells. HBL-100 was used as a negative screen to identify ER negative antibodies. HMFGM isolated from normal human milk was also used to select against normal breast epithelial surface components using a standard solid phase RIA (Tsu and Herzenberg (1980) supra.).

The final screening criteria were based on direct visualization of antigen distribution in paraffin slides using the immunoperoxidase technique for detection of antigens.

Second generation monoclonal antibodies were produced as above, except that the mice were immunized with antigen isolated from either MCF-7 tissue culture medium (fusion series 10 antibodies) or a membrane extract from 186-NWT cells (fusion series 7 antibodies). The antigens were isolated using an immunoaffinity column prepared with UCD/AB 6.11 antibodies, as described below. Screening procedures for the second generation antibodies were as follows. Selection of the second generation antibodies was based on reactivity in solid-phase RIA, Western Blots and immunoperoxidase (see below for details).

Immunodiffusion

The MCA's were isotyped using the double diffusion method of Ouchterlony and Nilsson (1973) in: Handbook of Experimental Immunology, Weir, ed. Blackwell, London, (chapter 19). Supernatants from each clone and ascites fluid diluted 1:100 in PBS (0.9% NaCl, 10 mM NaPO$_4$, pH 7.5) were reacted against antisera specific for each immunoglobulin class: IgM, IgG1, IgG2a, IgG3, and IgA. Class specific antisera were purchased from Miles Laboratories, Inc., Elkhart, Ind.

Live Cell Solid Phase RIA

Cells were harvested from 75 cm$^2$ tissue culture flasks by trypsinization, plated in 96 well tissue culture plates at 50,000 cells per well and incubated for 18 to 24 hours. All incubations were at 37° C. in 5% CO$_2$. Growth media were aspirated, 150 μl of growth media containing 0.08% sodium azide was added, and cells were incubated for 30 minutes. Cells were rinsed with Hank's balanced salt solution containing 5% calf sera and 0.08% sodium azide (wash buffer). Wash buffer (100 μl) was then added and the cells were incubated for 30 minutes. The cells were again rinsed with wash buffer and 50 μl of tissue culture fluid from a hybridoma culture or diluted ascites was added and incubated for 1 hour. The cells were then rinsed twice with wash buffer, and 50 μl ($2 \times 10^4$ cpm) of $^{125}$I-rabbit anti-mouse IgG was added and incubated for hour. The cells were washed two times with wash buffer and the positive wells were visualized by autoradiography.

Protein Analysis

Proteins were analysed by sodium dodecyl sulfate-polyacrylamide slab gel electrophoresis (SDS-PAGE), as described by Laemmli (1970) Nature 227:680–685, using a 4% acrylamide stacking gel with a 10% resolving gel, both containing 0.2% SDS. Samples were applied in 50 μl of sample buffer (63 mM TRIS pH 6.8, 10% glycerol, 5% 2-mercaptoethanol, 2.3% SDS) and were electrophoresed for four hours with a constant current of 20 mA. The molecular weights of proteins were estimated by their mobilities relative to standard proteins of known molecular weight.

Two-dimensional electrophoresis was performed as described by O'Farrell (1975) J. Biol. Chem. 250:4007–4021, except SDS-PAGE in the second dimension was as described above. Either 40 μl of immunoaffinity purified tissue culture fluid (evaporated to dryness and redissolved in lysis buffer) or 40 μl of cellular proteins dissolved in lysis buffer (1 confluent 100 mm petri dish dissolved in 2 ml of lysis buffer) were analysed.

Protein concentration was determined using a dye binding assay (Bio-Rad Laboratories, Richmond, CA).

Western Blots

To characterize the antigen identified by the antibody, a modification of the Western blot as described by Towbin, et al. (1979) Proc. Natl. Acad. Sci. U.S.A. 76:4350–4354 was used in which the proteins are transferred from SDS-PAGE gels to nitrocellulose filters and identified by the MCA. After transfer to the nitrocellulose filters, excess protein binding sites were blocked by soaking the filters in PBS containing 3% BSA. The antigen was located by incubating the sheet in 30 ml of PBS containing 1% BSA and $1-2 \times 10^7$ cpm of iodinated antibody for one hour. The filter was then rinsed, dried and autoradiographed. As little as 100 pg of protein can be detected with this procedure.

Analysis of Labelled Proteins

Cells were grown for 10 days in 5% calf serum treated with DCC to remove steroid hormones. Two days prior to testing, cells were trypsinized and plated at $4 \times 10^6$ cells per 100 mm petri dish. After 24 hours, estradiol was added to the media to attain concentrations of 0, 1, 10, and 100 nM estradiol. The media was changed after 24 hours. After 48 hours of hormone treatment, the cells were washed twice with Hank's balanced salt solution. Serum free media, hormone supplemented as above, containing 10% of the normal methionine concentration plus 200 μCi/ml of $^{35}$S-methionine was added. The cells and media were harvested after 6–12 hours incubation.

Immunoperoxidase Staining

The immunoperoxidase staining procedure used was a modification of the avidin-biotin immunoperoxidase technique of Hsu et al. (1981) J. Histochem. Cytochem. 29:577-580 as described by Horan-Hand et al. (1983) Cancer Res. 43:728-735.

Immunoaffinity Chromatography

Sepharose® 4B (Pharmacia Fine Chemicals, Piscataway, New Jersey) was activated with cyanogen bromide as described by March et al. (1974) Anal. Biochem. 60:149-152. Antibodies were purified from ascites by precipitation in 40% ammonium sulfate at 4° C. overnight. The precipitate was dissolved in and dialysed against 0.2 M $NaPO_4$, pH 7.3. One volume of activated Sepharose®, which had been filtered down to a compact cake, was added to 1.5 volumes of antibody solution (2 mg protein/ml). Antibody was coupled for 16 hours at 4° C. with gentle mixing. The Sepharose® was again filtered to a compact cake, washed with three volumes of water and added to 1.5 volumes of 1M ethanolamine, pH 9, to block unreacted sites. This reaction was allowed to proceed for two hours at 27° C. The Sepharose® was then washed with ten volumes each of phosphate buffer (0.1M $NaPO_4$, pH 7.3, 1.0M NaCl), 0.1M acetic acid, and phosphate buffer again in that order. The resin was stored at 4° C. in phosphate buffer with 0.1% sodium azide.

The affinity resin was poured into 0.2-1.0 ml columns, stripped with five column volumes of 6M guanidine-HCl pH 1.5, and rinsed with at least ten volumes of PBS before use. Tissue culture fluid was collected and 2 mM EDTA and phenyl-methyl-sulfonyl fluoride added to inhibit proteolysis. Debris was removed by centrifugation at 5000 X g for 20 minutes followed by filtration through glass wool and 0.22 micron filters. The sample was passed through a 1 ml column of Sepharose® 4B before being passed through the affinity column at 20-30 ml/hour at 4° C. Nonspecifically bound protein was eluted with 10-20 ml of 0.5M urea in PBS. Antigen was eluted with four column volumes of 6M guanidine-HCl pH 1.5, the eluent neutralized, and dialysed.

Iodination of Antibodies

Antibodies were iodinated by a chloramine T method (McConahey et al. (1980) Methods Enzymol. 70:210-213) to a specific activity of approximately 2 $\mu Ci/\mu g$. Reaction products were separated on a 1 cm by 30 cm column of Sephadex® G-25 in PBS with 1% BSA and were stored at $-70°$ C. until use.

Results

1. Production and Characterization of Monoclonal Antibodies

The autoradiographic binding pattern in the live cell RIA was the basis of the initial selection of MCA. Eighty-seven out of 288 wells from the initial fusion contained hybrid colonies that produced antibody against the MCF-7 cell line. Twenty-two of these colonies were chosen for expansion and further characterization. Nine colonies were cloned by limiting dilution. From these, two antibodies designated UCD/AB 6.01 and UCD/AB 6.11 were chosen for further characterization.

The specificity of UCD/AB 6.11 for MCF-7 was demonstrated by the Western blot technique. UCD/AB 6.11 bound to two SDS-PAGE bands in MCF-7 extracts but did not show any binding to HBL-100, NWT-186 HWT extracts or to HMFGM. For comparison, another clone, designated UCD/AB 6.13, showed binding to all three cell lines but not the HMFGM.

Detection of cellular antigens in paraffin sections using the avidin-biotin immunoperoxidase technique was performed to assure that the MCA's were binding human breast antigens and not just tissue culture artifacts of MCF-7.

The distribution of the antigens identified by UCD/AB 6.11 in normal, dysplastic and malignant breast tissue were determined using formalin and B-5 fixed tissue. B-5 fixation gave the better cytological detail.

Using avidin-biotin immunoperoxidase staining, UCD/AB 6.11 was found to bind to normal prelactating epithelial cells, but not with normal myoepithelium, stroma, or luminal secretory products. The antigen detected by UCD/AB 6.11 was primarily localized in supranuclear granules. This antigen had a patchy distribution between globules so that a positively staining globule was often found adjacent to a negatively staining globule. In many cases, adjacent cells within an individual globule were alternatively positive and negative.

Paraffin sections of 90% (18/20) of the breast cancer cells stained with immunoperoxidase were positive for UCD/AB 6.11. Most of the malignant cells in a given tissue section stained. The staining pattern was generally diffuse and cytoplasmic, although granular and surface staining were also observed. Staining was much more intense in the tumor cells than in adjacent normal cells. Staining was also more intense in metastatic tumor cells than in primary breast tumor cells. These results indicate that there is increased production of the antigen in the metastatic breast cancer cells.

Some but not all mammary dysplasias (fibrocystic disease) were stained with UCD/AB 6.11.

Second generation monoclonal antibodies resulting from immunization with antigen isolated by immunochromatography with 6.11 antibody from MCF-7 tissue culture medium were designated series 10. The particular antibodies selected for further characterization and testing were UCD/PR 10.02, UCD/PR 10.11, and UCD/PR 10.12. UCD/PR 10.02 is a murine IgM which reacts with type 18 cytokeratin, but does not inhibit binding of UCD/AB 6.11 or UCD/PR 10.11 to the antigen recognized by UCD/AB 6.11 (6.11 antigen). UCD/PR 10.11 is a murine IgG which reacts with the 6.11 antigen as well as type 8 cytokeratin and, to a lesser extent, with type 18 cytokeratin. UCD/PR 10.12 is a murine IgM which reacts with the 6.11 antigen.

Second generation monoclonal antibodies resulting from immunization with antigen [isolated by immunochromatography with 6.11 antibody] from 186-NWT cells were designated series 7. One particular antibody, designated UCD/PR 7.01, was found to be specific for myoepithelial cells.

2. Cell Surface Antigen

Iodination of the cell surface proteins of live cells by lactoperoxidase followed by immunoprecipitation was used to further characterize the cell surface location of the antigen identified by UCD/AB 6.11. This data showed that the antigen is located on the cell surface when the cells are grown either with or without estradiol.

3. Reactivity of Antibodies with Different Keratin-related Proteins

Three types of intracellular keratin-related proteins (related to Types 8, 18 and 19) were identified in the MCF-7 mammary carcinoma cell line. These proteins were estimated to have molecular weights of about 52, 46, and 40 kd and isoelectric points in the range from 6.1–6.0, 5.8–5.3, and 5.2–5.0, respectively. The multiple isoelectric forms observed are believed to be due at least in part to varying phosphorylation of the keratins. Immunoblots using anti-keratin monoclonal antibodies resulted in different patterns of binding for each antibody against each protein type. For example, the 35 β H11 antibody recognized all three MCF-7 cell keratin-related proteins, whereas AE1, UCD/AB 6.01, UCD/AB 6.11 and UCD/PR 10.11 each distinguished between the various protein types. See Table 1.

TABLE 1

| Antibody | Reactivity* | | |
|---|---|---|---|
| | Type 8 | Type 18 | Type 19 |
| AE1 | ± | ± | ++++ |
| 35 βH11 | ++++ | ++++ | ++++ |
| UCD/AB 6.11 | ± | ++++ | 0 |
| UCD/AB 6.01 | ++++ | ± | ± |
| UCD/PR 10.11 | ++++ | ± | 0 |
| UCD/PR 10.02 | + | +++ | 0 |

*Based on reactivity in two-dimensional Western Blots (see above).

4. Tissue Distribution of Epitopes Recognized by 6.11 and 10.11

In order to determine the tissue distribution of the epitopes recognized by monoclonal antibodies UCD/AB 6.11 and UCD/PR 10.11, and to evaluate the utility of these antibodies in immunodiagnosis, large numbers of formalin or B5-fixed paraffin tissue sections were screened by the avidin-biotin immunoperoxidase technique. The results are set forth in Table 2 below. In histologically normal tissues, both antibodies stained simple epithelial including mammary, sweat, and salivary glands, gastric and colonic mucosa, and kidney distal tubules. Both antibodies failed to react with neural and blood elements, although UCD/AB 6.11 (but not UCD/PR 10.11) often reacted weakly with a component of smooth muscle.

TABLE 2

| Tissue Stained | Reactivity (positive/total) | | Total Samples Examined |
|---|---|---|---|
| | 6.11 | 10.11 | |
| I. Breast | | | |
| A. Normal | | | |
| resting | 3/3 | 3/3 | 3 |
| prelacting | 2/2 | 2/2 | 2 |
| B. Abnormal | | | |
| Benign | | | |
| fibroadenoma | 5/6 | 6/6 | 6 |
| fibrocystic | 3/5 | 4/5 | 5 |
| apocrine metaplasia | 2/3 | 3/3 | 3 |
| dysplasia | 1/1 | 1/1 | 1 |
| Malignant | | | |
| adenocarcinoma | 6/7 | 5/7 | 7 |
| breast ca. | 0/4 | 3/4 | 4 |
| metastases TOTAL | | | 31 |
| II. Non-Breast | | | |
| A. Normal | | | |
| stomach | | | |

TABLE 2-continued

| Tissue Stained | Reactivity (positive/total) | | Total Samples Examined |
|---|---|---|---|
| | 6.11 | 10.11 | |
| chief cells | 3/3 | 0/3 | 3 |
| pariental cells | 3/3 | 3/3 | |
| lumenal epithelium | 3/3 | 3/3 | |
| jejunum | 1/1 | 1/1 | 1 |
| colon | 2/3 | 3/3 | 3 |
| muscle | | | 5 |
| skeletal | 0/4 | 0/4 | |
| cardiac | 0/1 | 0/1 | |
| trachea (fetal) | 1/1 | 1/1 | 1 |
| bronchus (fetal) | 1/1 | 1/1 | 1 |
| lung (fetal) | 1/1 | 1/1 | 1 |
| lymph node | 0/3 | 0/3 | 3 |
| spleen (fetal) | 0/1 | 0/1 | |
| adrenal | 0/3 | 0/3 | 3 |
| kidney | | | 3 |
| proximal tubules | 4/4 | 0/4 | |
| distal tubules/ducts | 4/4 | 4/4 | |
| glomeruli | 0/4 | 0/4 | |
| fallopian tube | | | |
| mucosal | 2/3 | 3/3 | |
| mesothelial | 1/3 | 3/3 | |
| ovary (fetal) | | | |
| primordial | 0/1 | 1/1 | 1 |
| stroma | 1/1 | 0/1 | |
| liver | | | 3 |
| parenchyma | 1/3 | 3/3 | |
| bile duct | 0/3 | 3/3 | |
| pancreas | | | 2 |
| islets | 0/2 | 0/2 | |
| acini | 2/2 | 0/2 | |
| ducts | 2/2 | 2/2 | |
| salivary gland | 1/2 | 2/2 | 2 |
| thyroid (fetal) | 0/1 | 0/1 | 1 |
| sweat gland | | | 4 |
| secretory | 4/4 | 4/4 | |
| excretory | 4/4 | 0/4 | |
| TOTAL | | | 40 |
| B. Abnormal | | | |
| colon carcinoma | 0/2 | 1/2 | 2 |
| squamous cell carcinoma | 1/1 | 0/1 | 1 |
| ganglionic neuroblastoma | 0/1 | 0/1 | 1 |
| seminoma | 0/1 | 0/1 | 1 |
| thyroid carcinoma | 0/1 | 1/1 | 1 |
| benign prostate hyperplasia | 0/1 | 1/1 | 1 |
| melanoma | 0/1 | 0/1 | 1 |
| TOTAL | | | 8 |

5. Epitope Distribution on Live Cells

Indirect immunofluorescence on live, intact MCF-7 cells was performed to visualize surface binding to cell surface epitopes. UCD/AB 6.01 and UCD/AB 6.11 identified punctate antigens which were dispersed over the entire cell surface with concentrations in regions of cell to cell contact. The cell surface epitopes were readily removed by light trypsin treatment, showed no evidence of patching or capping, and were present when cells were grown in either serum-containing or serum-free medium. The epitopes recognized by UCD/PR 10.11, 35βH11 and AE1, however, could not be detected in analogous indirect immunofluorescence experiments.

6. Characterization of Secreted 6.11 Antigen

Antigens related to keratin can also be found as soluble proteins in neoplastic mammary tissue culture media. Culture fluid from the MCF-7, T47D, and SK-BR 3 human mammary cell lines have each been found to contain keratin-like immunoreactivity. Four out of five monoclonal antibodies tested bind to the antigen from MCF-7 culture supernatants (Table 3), and the antigen has a molecular weight range of 40–46 kilodaltons and an isoelectric point of 5.0–5.2. Additional experiments indicated that the MCF-7 tissue culture antigen has a sedimentation coefficient of 3.6S and a buoyant density of 1.25 g/cm$^3$.

TABLE 3

| Antibody | Reactivity with MCF-7 Antigen 6.11 |
|---|---|
| UCD/AB 6.01 | − |
| UCD/AB 6.11 | + |
| UCD/PR 10.11 | + |
| AE1 | + |
| 35βH11 | + |

This MCF-7 extracellular antigen thus appears to be related to intracellular cytokeratin. First, antibodies raised against non-mammary keratins (such as 35βH11 and AE1) recognize the antigen. Second, when hybridomas are produced from mice immunized with the immunoaffinity-purified MCF-7 tissue culture fluid antigen, the resulting antibodies (such as UCD/PR 10.11) are broadly reactive with non-mammary keratins. Third, the amino acid composition of the purified MCF-7 antigen closely approximates that found for other keratins, particularly in that glycine and glutamic acid-glutamine residues comprise 25%–30% of the total amino acids in the protein. See Table 4.

TABLE 4*

| Amino Acid | Type 18 Keratin (46 kd) | Type 8 Keratin (52 kd) | MCF-7 Antigen 6.11 (40–46 kd) |
|---|---|---|---|
| Asp(+Asn) | 9.88% | 8.19% | 10.3% |
| Thr | 4.24 | 4.00 | 5.47 |
| Ser | 8.96 | 10.39 | 10.94 |
| Glu(+Gln) | 13.95 | 12.14 | 14.7 |
| Gly | 16.13 | 16.02 | 11.76 |
| Ala | 6.38 | 5.82 | 8.8 |
| Val | 5.82 | 6.49 | 6.05 |
| Ile | 4.68 | 6.00 | 4.39 |
| Leu | 7.52 | 8.94 | 9.37 |
| Tyr | 3.36 | 3.54 | 2.66 |
| Phe | 2.75 | 2.74 | 2.67 |
| His | 1.88 | 1.87 | 1.67 |
| Lys | 3.60 | 5.31 | 6.43 |
| Arg | 4.72 | 4.39 | 5.32 |
| Pro | 3.94 | — | 3.45 |
| Met | 0.17 | 4.18 | 1.2 |
| Trp | ND** | ND** | ND** |
| Cys | ND** | ND** | ND** |

*All values are subject to errors in measurement.
**Not Determined.

7. Serum Assay for Extracellular Cytokeratin

UCD/AB 6.11 was empolyed in a radioimmunoassay to detect the presence of extracellular cytokeratin in both normal serum and serum from patients suffering from breast cancer. The assay was a modification of the two-site immunoradiometric assay (IRMA) described by Miles et al. (1973) in: "Radioimmunoassays and Related Procedures in Medicine," International Atomic Energy Agency, Vienna, Austria, pp. 149–164, Vol. 1. Purified monoclonal antibody UCD/AB 6.11 was adsorbed on plastic microtiter plate wells. After adsorption, sample serum was placed into each well. If the extracellular cytokeratin was present in the serum sample, UCD/AB 6.11 bound to the solid phase reacted to capture the cytokeratin. Excess purified rabbit IgG antibody specific for a different epitope on the cytokeratin was then introduced to the microtiter wells where it reacted with the bound cytokeratin (if any). Excess $^{125}$I radiolabelled protein A was then introduced to the wells where it reacted with the rabbit IgG. After washing to remove unbound labelled protein A, the amount of radioactivity in each well was determined. The amount of extracellular cytokeratin was thus directly proportional to the amount of bound radioactivity. Absolute amounts of cytokeratin were determined from a previously prepared standard curve.

When normal serum was assayed for the presence of extracellular cytokeratin, values obtained ranged from 140 to 3260 CPM, corresponding to 0.02 μg/ml to 0.82 μg/ml. For breast cancer patients, the values were 340 to 10,800 CPM, corresponding to 0.05 μg/ml to 33.4 μg/ml. Choosing 1000 CPM as an arbitrary cut-off, two out of 14 (14%) of normal serum samples were positive. For breast cancer patients, 30 out of 83 (36%) were positive. Thus, the presence of extracellular cytokeratin in serum is significantly elevated in patients suffering from epithelial tumors, such as breast cancer.

In accordance with the subject invention, accurate and sensitive assay are provided for detecting the presence of a particular 42 to 48 kd cell protein and a related 40 to 46 kd serum protein in biological samples. The method is particularly useful for identifying those breast tumors which are responsive to estrogen therapy. The method is also useful for identifying such estrogen-sensitive breast tumors which have metastasized from the breast, and for screening patient's sera for such tumors.

Although the foregoing invention has been described in some detail by way of illustration and example for purposes of clarity of understanding, it will be obvious that certain changes and modifications may be practiced within the scope of the appended claims.

What is claimed is:

1. A method for detecting neoplastic epithelial cells in a patient, comprising detecting soluble extracellular cytokeratin in a serum sample of said patient, said extracellular cytokeratin being structurally and immunologically related to intracellular cytokeratin and characterized by a blocked N-terminus.

2. A method as in claim 1, wherein the extracellular cytokeratin is further characterized by reactivity with antibodies obtained from hybridoma cell lines UCD-/AB 6.11 or UCD/PR 10.11, A.T.C.C. Nos. HB 8458 and HB 8694, respectively.

3. A method as in claim 1, wherein the extracellular cytokeratin is immunologically related to Type 8 and Type 18 intracellular cytokeratin.

4. A method according to claim 1, wherein the sample is urine.

5. A method as in claim 1, wherein the extracellular cytokeratin is related to intracellular cytokeratin from mammary epithelial cells and has a molecular weight in the range from 40 to 46 kd.

6. A method according to claim 5, wherein the sample is urine.

7. A method for detecting neoplastic epithelial cells in a human biological sample, comprising combining the sample with monoclonal antibodies specific for an epitopic site recognized by antibodes obtained from hybridoma cell lines UCD/AB 6.11 or UCD/PR 10.11, A.T.C.C. Nos. HB 8458 and HB 8694, respectively, and determining the formation of specific antibody-antigen complexes in said sample.

8. A method as in claim 7, wherein the sample is serum.

9. A method as in claim 7, wherein the sample is a tissue sample.

10. A method according to claim 7, wherein the sample is urine.

11. A method for screening metosttic neoplastic epithelial cells to determine the cellular origin of such cells, comprising:
exposing a sample of the neoplastic epithelial cells to a group of antibodies where individual antibodies within the group are capable of selectively reacting with ductal epithelial cells, secretory epithelial cells, myoepithelial cells, or combinations thereof;
determining which of the antibodies react with the neoplastic epithelial cells; and
determining the origin of the neoplastic epithelial cells based on the pattern of reactivity of the antibodies.

12. A method as in claim 11, wherein the epithelial cells are mammary epithelial cells.

13. A method as in claim 11, wherein the group of antibodies comprises a first antibody reactive with ductal epithelial cells but substantially less reactive with secretory epithelial cells and myoepithelial cells, a second antibody reactive with secretory epithelial cells but substantially less reactive with ductal epithelial cells and myoepithelial cells, and a third antibody reactive with myoepithelial cells but substantially less reactive with ductal epithelial cells and secretory epithelial cells.

14. A method as in claim 13, wherein the antibody reactive with ductal epithelial cells is obtained from hybridoma cell line UCD/PR 10.11, having ATCC identification number HB 8694.

15. A method as in claim 13, wherein the antibody reactive with secretory epithelial cells is obtained from hybridoma cell line UCD/AB 6.11, having ATCC identification number HB8458.

16. A kit for screening metastatic neoplastic epithelial cells to determine the cellular origin of such cells, comprising:
antibody reactive with ductal epithelial cells but substantially less reactive with secretory epithelial cells and myoepithelia cells:
antibody reactive with secretory epithelial cells but substantially less reactive with ductal epithelial cells and myoepithelial cells;
antibody reactive with myoepithelial cells but substantially less reactive with ductal epithelial cells and secretory epithelial cells; and
means for detecting the reaction of said antibodies with said neoplastic epithelial cells or extra-cellular cytokeratins therefrom.

17. A kit as in claim 16, wherein the epithelial cells are mammary epithelial cells.

18. A kit as in claim 16, wherein the antibody reactive with ductal epithelial cells is obtained from hybridoma cell line UCD/PR 10.11, having ATCC identification number HB8694.

19. A kit as in claim 16, wherein the antibody reactive with secretory epithelial cells is obtained from hybridoma cell line UCD/AB 6.11, having ATCC identification number HB8458.

20. Hybridoma cell line UCD/AB 6.11, American Type Culture Collection accession no. HB 8458.

21. Hybridoma cell line UCD/PR 10.11, American Type Culture Collection accession no. HB8694.

22. Antibodies from the hybridoma cell line UCD/PR 10.11, American Type Culture Collection accession no. HB 8694.

23. Hybridoma cells producing monoclonal antibodies specific for an epitope present on an approximately 40 to 46 kd extracellular cytokeratin released by human mammary epithelial cells, said epitope being recognized by antibodies obtained from hybridoma cell lines UCD/AB 6.11 or UCD/PR 10.11, A.T.C.C. Nos. HB 8458 and HB 8694, respectively.

24. Antibodies produced by hybridoma cells producing monoclonal antibodies specific for an epitope present on an approximately 40 to 46 kd extracellular cytokeratin released by human mammary epithelial cells, said epitope being recognized by antibodies obtained from hybridoma cell lines UCD/AB 6.11 or UCD/PR 10.11, A.T.C.C. Nos. HB 8458 and HB 8694, respectively.

25. A method for distinguishing carcinoma tumors from tumors of non-epithelial origin, comprising combining a sample of tumor cells with monoclonal antibody obtained from hybridoma cell line UCD/PR 10.11, having ATCC identification number HB 8694, or with other monoclonal antibody having at least equivalent affinity for the epitopic site recognized by antibody obtained from UCD/PR 10.11, and determining the formation of specific antibody-antigen complexes in said sample.

26. An extracellular soluble cytokeratin secreted by neoplastic epithelial cells and reactive with antibodies obtained from hybridoma cell lines UCD/AB 6.11 or UCD/PR 10.11, A.T.C.C. Nos. HB 8458 and HB 8694, respectively, said cytokeratin being substantially free from other serum proteins.

27. An extracellular soluble cytokeratin as in claim 26, having a molecular weight in the range from 40 to 46 kd.

28. An extracellular soluble cytokeratin as in claim 27, having a blocked N-terminus.

29. A extracellular soluble cytokeratin secreted by neoplastic mammary epithelial cells, said cytokeratin having a blocked N-terminus, a molecular weight in the range from 40 to 46 kd, and being substantially free from other serum proteins.

30. Antibodies from the hybridoma cell line UCD/AB 6.11, American Type Culture Collection accession no. HB 8458.

31. A method for screening neoplastic epithelial cells to determine the origin of such cells, comprising:
exposing a sample of the neoplastic epithelial cells to a group of antibodies wherein individual antibodies within the group are capable of selectively reacting with ductal epithelial cells, secretory epithelial cells, myoepithelial cells, or a combination thereof, wherein at least one of said antibodies is an antibody produced by cell line UCD/PR 10.11, UCD/AB 6.11, or UCD/AB6.01, having ATCC identification numbers HB 8694, and HB 8458 and HB 8693 respectively;
determining which of the antibodies react with the neoplastic epithelial cells; and
determining the origin of the neoplastic epithelial cells based on the pattern of reactivity of the antibodies.

32. A method for screening neoplastic epithelial cells to determine the origin of such cells, comprising:
exposing a sample of the neoplastic epithelial cells to a group of antibodies wherein individual antibodies within the group comprise a first antibody reactive with ductal epithelial cells but being substantially less reactive with secretory epithelial cells and myoepithelial cells, a second antibody reactive with secretory epithelial cells but being substantially less reactive with ductal epithelial cells and myoepithelial cells, and a third antibody reactive with myoepithelial cells but being substantially less reactive with ductal epithelial cells and secretory epithelial cells, or combinations thereof;

determining which of the antibodies react with the neoplastic epithelial cells; and determining the origin of the neoplastic epithelial cells based on the pattern of reactivity of the antibodies.

33. A kit for screening neoplastic epithelial cells to determine the origin of such cells, comprising:
  (a) antibody selected from the group consisting of antibody reactive with ductal epithelial cells but being substantially less reactive with secretory epithelial cells and myoepithelial cells, antibody reactive with secretory epithelial cells but being substantially less reactive with ductal epithelial cells and myoepithelial cells, antibody reactive with myoepithelial cells but being substantially less reactive with ductal epithelial cells and secretory epithelial cells, and combinations thereof; and
  (b) means for detecting the reaction of said antibodies with said neoplastic epithelial cells.

34. Antibody selected from the group consisting of antibody reactive with ductal epithelial cells but being substantially less reactive with secretory epithelial cells and myoepithelial cells, antibody reactive with secretory epithelial cells but being substantially less reactive with ductal epithelial cells and myoepithelial cells, antibody reactive with myoepithelial cells but being substantially less reactive with ductal epithelial cells and secretory epithelial cells, and combinations thereof, wherein at least one of said antibodies is an antibody produced by cell line UCD/PR 10.11, UCD/AB 6.11, or UCD/AB6.01 having ATCC identification numbers HB 8694, HB 8458 and HB 8693 respectively.

* * * * *